(12) United States Patent
Roorda et al.

(10) Patent No.: US 7,175,873 B1
(45) Date of Patent: Feb. 13, 2007

(54) RATE LIMITING BARRIERS FOR IMPLANTABLE DEVICES AND METHODS FOR FABRICATION THEREOF

(75) Inventors: Wouter E. Roorda, Palo Alto, CA (US); Syed F. A. Hossainy, Fremont, CA (US); Ni Ding, San Jose, CA (US); Fuh-Wei Tang, Temecula, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/198,898

(22) Filed: Jul. 18, 2002

Related U.S. Application Data

(63) Continuation-in-part of application No. 09/894,293, filed on Jun. 27, 2001, now abandoned.

(51) Int. Cl.
*A61L 33/10* (2006.01)
(52) U.S. Cl. ..................... 427/2.14; 427/2.25
(58) Field of Classification Search ............... 427/2.12, 427/2.14, 2.25
See application file for complete search history.

(56) References Cited

U.S. PATENT DOCUMENTS

| | | | |
|---|---|---|---|
| 4,931,287 A | 6/1990 | Bae et al. ................... 424/484 |
| 4,977,901 A | 12/1990 | Ofstead ....................... 128/772 |
| 5,112,457 A | 5/1992 | Marchant ..................... 204/165 |
| 5,328,471 A | 7/1994 | Slepian ........................ 604/101 |
| 5,455,040 A | 10/1995 | Marchant ..................... 424/496 |
| 5,464,650 A | 11/1995 | Berg et al. .................... 427/2.3 |
| 5,578,073 A | 11/1996 | Haimovich et al. ............. 623/1 |
| 5,605,696 A | 2/1997 | Eury et al. .................... 424/423 |
| 5,667,767 A | 9/1997 | Greff et al. ............... 424/9.411 |
| 5,670,558 A | 9/1997 | Onishi et al. ............... 523/112 |
| 5,700,286 A | 12/1997 | Tartaglia et al. ................ 623/1 |
| 5,716,981 A | 2/1998 | Hunter et al. ................ 514/449 |
| 5,824,049 A | 10/1998 | Ragheb et al. .................. 623/1 |
| 5,830,178 A | 11/1998 | Jones et al. .................... 604/49 |
| 5,837,313 A | 11/1998 | Ding et al. ................. 427/2.21 |
| 5,851,508 A | 12/1998 | Greff et al. ............... 424/9.411 |
| 5,858,746 A | 1/1999 | Hubbell et al. ............. 435/177 |
| 5,858,990 A | 1/1999 | Walsh .......................... 514/44 |
| 5,865,814 A | 2/1999 | Tuch .......................... 604/265 |
| 5,873,904 A | 2/1999 | Ragheb et al. .................. 623/1 |
| 5,971,954 A | 10/1999 | Conway et al. ............... 604/96 |
| 5,980,928 A | 11/1999 | Terry .......................... 424/427 |
| 5,980,972 A | 11/1999 | Ding ......................... 427/2.24 |

(Continued)

FOREIGN PATENT DOCUMENTS

EP  0 665 023  8/1995

(Continued)

*Primary Examiner*—D. Lawrence Tarazano
(74) *Attorney, Agent, or Firm*—Squire, Sanders & Dempsey L.L.P.

(57) ABSTRACT

A method of coating an implantable medical device, such as a stent, is disclosed. The method includes applying a formulation on a first polymer layer containing a therapeutic substance to form a second layer. The formulation can contain a highly hydrophobic polymer or a solvent which is a poor solvent for the drug or the polymer of the first layer. The formulation can have a low surface tension value or a high Weber number value.

19 Claims, 2 Drawing Sheets

U.S. PATENT DOCUMENTS

| | | | |
|---|---|---|---|
| 5,997,517 A | 12/1999 | Whitbourne | 604/265 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,254,632 B1 | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,913 B1 | 8/2001 | Wright et al. | 623/1.42 |
| 6,319,520 B1 | 11/2001 | Wuthrich et al. | 424/482 |
| 6,344,035 B1 | 2/2002 | Chudzik et al. | 604/265 |
| 2002/0005206 A1 * | 1/2002 | Falotico et al. | 128/898 |
| 2004/0106987 A1 * | 6/2004 | Palasis et al. | 623/1.42 |
| 2004/0117006 A1 * | 6/2004 | Lewis et al. | 623/1.42 |

FOREIGN PATENT DOCUMENTS

| | | | |
|---|---|---|---|
| EP | 0 923 953 | * | 6/1999 |
| EP | 0 970 711 | | 1/2000 |
| WO | WO 00/12147 | | 3/2000 |
| WO | WO 00/64506 | | 11/2000 |
| WO | WO 01/01890 A1 | | 1/2001 |
| WO | WO 02/47731 | | 6/2002 |
| WO | WO 2004/009145 | * | 1/2004 |

* cited by examiner

RATE LIMITING BARRIERS FOR IMPLANTABLE DEVICES AND METHODS FOR FABRICATION THEREOF

CROSS REFERENCE

This is a continuation-in-part of U.S. patent application Ser. No. 09/894,293, filed on Jun. 27, 2001 now abandoned.

BACKGROUND OF THE INVENTION

1. Field of the Invention

This invention relates to the field of implantable medical devices. Particularly, this invention is directed to coatings for drug delivery devices, such as drug eluting vascular stents.

2. Description of the State of the Art

In the treatment of vascular disorders, such as arteriosclerosis, intracoronary stents such as balloon expandable or self-expandable stents are now a standard adjunct to balloon angioplasty. Although a significant innovation for eliminating vasospasm, tacking intimal flaps to the vessel wall, and reduce negative remodeling, restenosis of the vessel following balloon angioplasty and stent replacement remains a persistent problem. Accordingly, stents are being modified to provide biological therapy for the treatment of restenosis.

Being made of a metallic material, such as stainless steel, bare stents have to be modified so as to provide an appropriate means for the deliver a drug. A polymeric coating on the surface of a stent is one method for providing a vehicle for the local delivery of a drug. A conventional coating used to achieve local drug delivery via stent can include a three-layer structure, as illustrated by FIG. 1. The three layer structure includes a drug-polymer layer 3 serving as a reservoir for the drug, a primer polymer layer 2 for improving the adhesion of the drug-polymer layer 3 to the surface of the stent 1, and a topcoat polymer layer 4 for reducing the rate of release of the drug from the drug polymer layer 3. The medicine to be administered will have a sustained release profile from drug-polymer layer 3 through the topcoat polymer layer 4.

For the effective treatment of restenosis, it is important to maintain the concentration of the drug at the treatment site at a therapeutically effective level for an acceptable period of time. Hence, controlling a rate of release of the drug from the stent is important, especially in such a way so as to provide a sustained, relatively constant, long-term release of the drug from the polymer matrix. In view of the foregoing, improved coatings and methods of fabricating the coatings for reducing the rate of release a therapeutic substance from stents are desired. The coatings should prolong the residence time of the drug in the patient, among other suitable characteristics, such as a steady rate of release.

SUMMARY

In accordance with one embodiment, a method for coating an implantable medical device, such as a stent, is disclosed comprising: forming a first layer on the device, the first layer comprising a first polymer and a therapeutic substance incorporated therein; and applying a formulation on the first layer to form a second layer, the formulation comprising a second polymer and a solvent, the solvent being a poor solvent for the therapeutic substance or the first polymer for preventing a significant migration of the therapeutic substance out from the first layer during the application of the formulation. The solubility of the therapeutic substance or the first polymer in the solvent can be less than about 1.0 mass % at room temperature. The second polymer can also be highly hydrophobic, e.g., having the solubility parameter in water of about less than 11 $(cal/cm^3)^{1/2}$. The formulation can have a low value of surface tension or a high value of a Weber number. For example, the surface tension can be about 15 to about 30 $dyn/cm^2$, and the value of the Weber number can be about 2,500 to about 45,000.

In accordance with another embodiment, a method for coating an implantable medical device, such as a stent, is provided comprising: forming a first layer on the device, the first layer comprising a first polymer and a therapeutic substance; and applying a formulation including a second polymer on the first layer to form a second layer, wherein the second polymer is more hydrophobic than the first polymer. The formulation can additionally include a solvent, wherein the solvent is not capable of significantly causing the migration of the therapeutic substance out from the first layer. The formulation can have a low value of surface tension or a high value of Weber number.

In accordance with another embodiment, a method for coating an implantable medical device, such as a stent, is provided comprising: forming a first layer on the device, the first layer comprising a polymer and a therapeutic substance; and applying a formulation on the first layer to form a second layer, the formulation having a surface tension value of about 15 to about 30 $dyn/cm^2$ or a Weber value of about 2,500 to about 45,000. The formulation includes a polymer dissolved in a solvent.

In accordance with another embodiment, a coating for an implantable medical device, such as a stent, is provided comprising: a first layer comprising a first polymer and a therapeutic substance incorporated therein; and a second layer disposed directly or indirectly over the first layer, the second layer comprising a second polymer having a greater degree of hydrophobicity than the first polymer. The first polymer can be poly(ethylene-co-vinyl alcohol) and the second polymer can be poly(butyl methacrylate), poly(ethyl methacrylate), poly(2-ethylhexyl methacrylate), poly(ethylene-co-vinyl acetate), poly(vinylidene fluoride), ELASTEON block-copolymer, C-FLEX tri-block copolymer, BIONATE polymer or blends thereof.

In accordance with another embodiment, a method for coating an implantable medical device, such as a stent, is provided comprising: forming a first layer on the device, the first layer including a therapeutic substance; and applying a formulation on the first layer to form a second layer, the formulation comprising a solvent having an evaporation rate of at least three times greater than the evaporation rate of butyl acetate.

DETAILED DESCRIPTION

Figure 1:
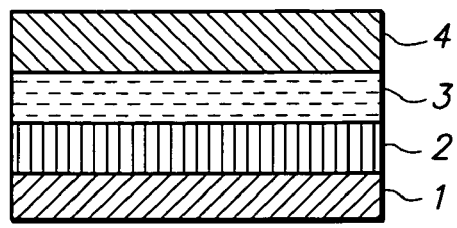
FIG. 1 schematically depicts a cross-section of a conventional multi-layered polymeric coating for stents.
Figure 2:
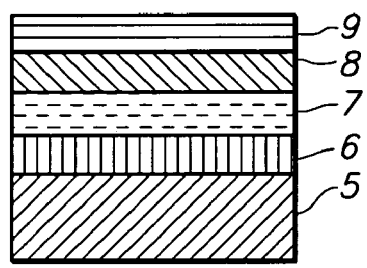
FIG. 2 schematically depicts a cross-section of an embodiment of a coating on a stent according to the present invention.

FIG. 2 illustrates a coated stent 5 according to one embodiment of the present invention. The coating comprises an primer layer 6, a drug-polymer or reservoir layer 7, a topcoat layer 8, and a finishing coat layer 9. The primer layer 6 and finishing coat layer 9 need not be including in the coating structure and are optionally provided. The topcoat layer 8 can be formed by the following methods:

(A) using a poor solvent in the topcoat formulation;

(B) using a fast-evaporating solvent in the topcoat formulation;

(C) making the topcoat layer 8 by using short spray cycles followed by rapid drying;

(D) using a very hydrophobic polymer in the topcoat layer 8; and (E) using the topcoat formulations with low surface tension and/or high Weber values.

A. Using a Poor Solvent in the Topcoat Formulation

The formulation for fabricating topcoat layer 8 includes at least one polymer and at least one solvent. The topcoat layer 8 can be applied directly on the drug-polymer layer 7 by spraying or dipping methods, as is known to one of ordinary skill in the art. Once the solvent used in the topcoat formulation comes in contact with the surface of the drug-polymer layer 7, the solvent often causes migration of the drug to the interface between the drug-polymer layer 7 and the topcoat layer 8, or into the topcoat membrane layer 8. Such migration can be the result of at least partial solubility of the drug in the solvent of the topcoat formulation. In addition, the solvent of the topcoat formulation may cause swelling of the polymer in the drug-polymer layer 7 leading to further acceleration of drug migration.

Drug migration to the outer most coating layers is undesirable in that it diminishes the effectiveness of the topcoat membrane layer 8 in controlling the release rate of the drug from the matrix. The migration of the drug can be eliminated or at least reduced by using a solvent, or a mixture of solvents, which will be adequate for dissolving the polymer of the topcoat formulation while being a poor solvent for the polymer and/or the drug used in the drug-polymer layer 7.

Consequently, in accordance with one aspect of the present invention, the solvent selected for the topcoat formulation is a poor solvent for the polymer and/or the drug used in the drug-polymer layer 7. Alternatively, if a mixture of solvents is used, the system as a whole should be a poor solvent for the polymer and/or the drug used in the drug-polymer layer 7.

"Poor solvent" is defined as a solvent in which only trace amounts of the polymer and/or the drug can be dissolved. The amounts are considered "trace amounts" for the purposes of the present invention if the solubility of the polymer and/or drug in that solvent is less than about 1.0% (mass) at room temperature, for example, between about 0.1% (mass) and about 0.5% (mass). The term "solubility" is defined as a mass of the polymer and/or drug contained in a solution which is in equilibrium with an excess of the polymer and/or drug. In other words, the solubility of a substance is the concentration of a solution that is saturated under the given conditions. The "concentration of a solution" is the amount of solute in a given amount of solvent or solution. A "saturated" solution is a solution in which the concentration of dissolved solute is equal to that which would be in equilibrium with un-dissolved solute under the given conditions, such as temperature.

Poor solvents that can be used for the topcoat formulation depend on the underlying polymer layer and the drug used. For example, the following solvents may be generally categorized as poor solvents: ethanol (EtOH); isopropanol (IPA); tetrahydrofuran (THF); pentane; a xylene (any of dimethylbenzenes), e.g., o-xylene; acetone; toluene; FLUX REMOVER AMS; NOVEC HFE (hydrofluoroether) fluids; and mixtures thereof. Those having ordinary skill in the art will choose other solvents if desired, so long as the selected solvent satisfies the definition of the "poor solvent" given above.

FLUX REMOVER AMS is a solvent manufactured by Tech Spray, Inc. of Amarillo, Tex. comprising about 93.7% of a mixture of 3,3-dichloro-1,1,1,2,2-pentafluoropropane having a formula $CF_3$—$CF_2$—$CHCl_2$ and 1,3-dichloro-1,1,2,2,3-pentafluoropropane having a formula $CF_2Cl$—$CF_2$—$CHFCl$, and the balance methanol, with trace amounts of nitromethane. NOVEC fluids are solvents based on hydrofuoroethers and are available from 3M Corp. of St. Paul, Minn.

The poor solvent can be a single solvent or a mixture of solvents. Alternatively, any other fluids for improving coating characteristics can be added to the system as long the other fluids do not result in an undesirable migration of the drug. Representative examples of such other fluids can include, for example, N,N-dimethylacetamide (DMAC), N,N-dimethylformamide, dimethylsulphoxide (DMSO), trifluoroethanol, and hexafluoroisopropanol.

There are no limitations on the type of active agents or drugs that can be included within the drug-polymer layer 7. For example, the active agent could be designed to inhibit the activity of vascular smooth muscle cells. The agent can be directed at inhibiting abnormal or inappropriate migration and/or proliferation of smooth muscle cells to inhibit restenosis. The active agent or the drug can include any substance capable of exerting a therapeutic or prophylactic effect for a patient. The drug may include small molecule drugs, peptides, proteins, oligonucleotides, and the like. Examples of drugs include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon; genetically engineered epithelial cells; rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin; tacrolimus; and dexamethasone.

While the poor solvents described above may be suitable for using in the topcoat formulations when some of these drugs are incorporated into the drug-polymer layer 7, for the other drugs alternative solvents may be required. Those having ordinary skill in the art will choose such alternative solvents among the solvents satisfying the definition of the "poor solvent."

Representative examples of suitable polymers that can be used to form a drug-polymer layer 7, the optional primer layer 6, and/or the topcoat membrane layer 8 include acrylic polymers and copolymers such as poly(butyl methacrylate) (PBMA), poly(ethylene-co-vinyl alcohol) (known as EVAL or EVOH), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane; poly (amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alpha-olefin copolymers, vinyl halide polymers and copolymers (such as polyvinyl chloride and polyvinylidene fluoride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Those having ordinary skill in the art should selected the appropriate combination of polymers and solvents for the fabrication of each of the layers so as to eliminate or minimize drug migration from the lower layer(s) into the upper layer(s).

B. Using a Fast-Evaporating Solvent to Fabricate the Topcoat Layer

According to another embodiment of the present invention, the solvent selected for the topcoat membrane formulation is a fast-evaporating solvent but is otherwise a suitable solvent, i.e., dissolves the polymer chosen for making the topcoat membrane layer 8. The polymer forming the topcoat membrane is dissolved in a solvent having a high rate of evaporation and the solution is applied (e.g., sprayed) over the drug-polymer layer 7 to form the topcoat layer 8.

Rate of evaporation of a solvent is a proportional comparative characteristic as it is compared to the rate of evaporation of butyl acetate. In other words, the rate of evaporation of butyl acetate is a standard used for comparing the rates of evaporation of other solvents. The rate of evaporation of butyl acetate has been assigned a dimensionless value of 100, according to a generally accepted rating system established by PPG Industries, Inc. of Pittsburgh, Pa. Therefore, for example, if a solvent has an evaporation rate of 250, it evaporates 2.5 times faster than butyl acetate. The term "fast-evaporating solvent" or a solvent having a "high rate of evaporation" is defined as a solvent with a rating of at least 300—or 3 times faster than the assigned evaporation rate of 100 for butyl acetate (e.g., a solvent with a rating of 500). Representative examples of suitable fast-evaporating solvents that can be used to make the topcoat membrane include acetone (evaporation rate 1448), hexane (910), methyl ethyl ketone (570), cyclohexane (550), heptane (430), and EtOH (330).

C. Using Short Spray Cycles Followed by Rapid Drying

According to yet another embodiment of the present invention, the topcoat layer 8 can be formed by using short, burst-like spray cycles followed by rapid drying. A topcoat formulation can be prepared by dissolving a polymer, for example PBMA, in a solvent or solvent mixture such as a mixture of methanol and cyclohexanone. The solvent mixture can contain between about 10 and 80 mass % of methanol, for example, about 60 mass % of EtOH, and the balance, cyclohexanone. The concentration of PBMA in the solvent mixture is between about 2 and 10 mass %. To deposit the topcoat membrane layer, the PBMA solution can be sprayed onto the drug-polymer layer 7 in a series of bursts, each burst lasting between about 0.5 seconds and 1.0 second, for example, about 0.75 seconds, followed by about 5 seconds of drying with warm air.

D. Using a Very Hydrophobic Polymer in the Topcoat Layer

According to another embodiment of the present invention, the polymer used to form the topcoat layer 8 can be partially or fully replaced with a highly hydrophobic polymer or blend of polymers. Between about 15% to 100% of the topcoat polymer can be replaced. Hydrophobicity is defined as the association of non-polar groups or molecules in an aqueous environment which arises from the tendency of water to exclude non-polar molecules. The term "hydrophobic" refers to a polymer that has a solubility parameter, in water, of less than 11 $(cal/cm^3)^{1/2}$. The lower the degree of solubility, the more hydrophobic the polymer is considered to be.

Examples of highly hydrophobic polymers that can be used according to the present invention include, but are not limited to, poly(butyl methacrylate) (PBMA), poly(ethyl methacrylate) (PEMA), poly(2-ethylhexyl methacrylate) (PEHMA), poly(ethylene-co-vinyl acetate) (PEVA), poly (vinylidene fluoride) (PVDF), ELASTEON polyurethane block-copolymer, C-FLEX tri-block copolymer, BIONATE polymer and blends thereof.

ELASTEON is a product of co-polycondensation of 4,4'-methylenebis(phenyl isocyanate) with butane-1,4-diol and a reaction of the isocyanate-diol adduct with polydimethylsiloxane (PDMS). PDMS can be hydroxyfunctional, for example, carbinol-terminated. ELASTEON is a block-copolymer manufactured by AorTech Biomaterials Co. of Chatswood, Australia. C-FLEX tri-block copolymer is a thermoplastic elastomer (styrene-ethylene/butylene-styrene block copolymer with poly(dimethylsiloxane), poly(propylene), mineral oil, antioxidant and other modifiers) manufactured by Concept Polymer Technologies. Inc. of Clearwater, Fla. BIONATE polymer is manufactured by The Polymer Technology Group Incorporated of Berkeley, Calif. BIONATE is a thermoplastic polycarbonate-urethane elastomer formed as the product of the reaction between a hydroxyl-terminated polycarbonate, an aromatic diisocyanate, and a low molecular weight glycol used as a chain extender.

The highly hydrophobic polymer can be dissolved in a solvent to make a solution having a concentration between, by way of example, about 1.5 and about 5.3 mass %. Any appropriate solvent or a mixture of solvents can be used, including any of the poor solvents described above. Other suitable solvents may include DMAC and DMSO. The topcoat formulation is then applied onto the drug-polymer layer 7 by any conventional method, e.g., by spraying.

E. Using the Topcoat Formulations with Low Surface Tension and/or High Weber Numbers According to yet another embodiment of the present invention, topcoat formulations having a low surface tension or a high Weber number can be used. When a topcoat formulation is atomized during spray application process, the inertial forces of the liquid jet and the atomizing gas act to break up the topcoat solution into small droplets. At the same time, the surface tension of the topcoat solution resists this break up, yielding large droplets which can create coating defects such as webbing and bridging between the stent struts. It is desirable to have a topcoat formulation with a low surface tension to not only facilitate formation of a conformal, defect free topcoat layer, but also to reduce the exposure of the solvent of the topcoat formulation to the drug-polymer layer 7. The reduction of the exposure of the solvent to the drug-polymer layer 7 is correlated to the reduction of the amount of the formulation for the topcoat layer 8 that is applied to the stent in order to achieve a topcoat layer of a desired thickness. By using a low-surface tension formulation, the quantity of the composition that is applied to the drug-polymer layer 7 can be reduced without comprising the thickness of the topcoat layer 8.

The ratio between the two forces is reflected in the dimensionless Weber number W:

$$W = V^2 \rho L / \sigma,$$

where V is velocity of the atomized droplets (m/s); $\rho$ is density of the droplets (kg/m$^3$); L is a characteristic length of the system, which, in the case of spraying, is the diameter of the liquid jet (m); and $\sigma$ is the surface tension of the topcoat formulation (J/m$^2$ or kg/s$^2$).

For the same application conditions, V and L are constant and $\rho$ changes very little because the solutions of the topcoat formulations are always very diluted. However, W is inversely correlated to $\sigma$. Accordingly, the desired topcoat formulation having a low value for $\sigma$ should have a high value for the Weber number W. The topcoat formulation according to the present invention can have a value for $\sigma$ within a range of between about 15 and about 30 dyn/cm$^2$ and the value for W between about 2,500 and about 45,000.

Both the polymer and the solvent of the topcoat formulation contribute to physical properties of the formulation. Therefore, to create a topcoat formulation having a low-surface tension and/or high Weber number, proper selection of both the polymer and the solvent of the topcoat formulation is important. Examples of appropriate polymers to be used in the topcoat formulations include EVAL, BIONATE and PBMA. Examples of appropriate solvents to be used to dissolve the polymers to make the low-surface tension and/or high Weber number topcoat formulations include DMSO, DMAC, THF, IPA, EtOH, cyclohexanone, acetone, xylene, pentane, fluorinated hydrocarbons and mixtures thereof. Those having ordinary skill in the art can derive appropriate polymer and solvent combinations which can fall within the Webber number range of the present invention.

According to any of the embodiments of the present invention, the rate of release of the drug from the drug-polymer layer 7 can be additionally controlled by cross-linking the polymer of the topcoat layer 8. The cross-linked polymer will have an increased molecular weight and increased density of the tri-dimensional polymer network which can further decelerate the process of the drug migration from the drug-polymer layer 7 and through the topcoat layer 8. To be cross-linked, the polymer of the topcoat membrane layer 8 should have appropriate reactive groups. For example, if EVAL is present in the topcoat membrane layer 8, it can be cross-linked via its hydroxyl groups. The cross-linking can be performed without adding any cross-linking agents, for instance, by using plasma, UV-radiation, electron beam radiation, or gamma radiation.

The above-discussed methods of controlling the rate of the release of the drug from the drug-polymer layer 7 can be combined and is not intended to be applicable solely separately. For example, a topcoat formulation including a highly hydrophobic polymer can be prepared with a poor solvent for the drug and/or the polymer of the drug-polymer layer 7. After the formulation has been applied onto the drug-polymer layer 7, the polymer of the topcoat membrane layer 8 can be additionally fortified by cross-linking reaction.

The coatings have been described with reference to a stent, e.g., balloon expandable or self-expandable stents. However, the coatings can also be used with a variety of other medical devices. Examples of implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

Embodiments of the present invention can be further illustrated by the following Examples.

Example 1

A first composition was prepared by mixing the following components:
(a) about 2.0 mass % of EVAL; and
(b) the balance, DMAC solvent.
EVAL has the general formula —[CH$_2$—CH$_2$]$_m$—[CH$_2$—CH(OH)]$_n$—. EVAL is a product of hydrolysis of ethylene-vinyl acetate copolymers and may also be a terpolymer including up to 5 molar % of units derived from styrene, propylene and other suitable unsaturated monomers. The first composition was applied onto the surface of a bare 12 mm TETRA stent by spraying and dried to form a primer layer. An EFD spray head was used, having a 0.014 inch fan nozzle with a feed pressure of about 0.2 atm (3 psi) and an atomization pressure of between about 1 atm and 1.3 atm (15 to 20 psi). The total amount of solids of the primer layer was about 40 micrograms (μg), corresponding to the thickness of about 0.3 to 0.6 micrometers (μm). "Solids" means the amount of the dry residue deposited on the stent after all volatile organic compounds (e.g., the solvent) have been removed.

A second composition was prepared by mixing the following components:
(c) about 3.0 mass % of EVAL;
(d) about 1.5 mass % of estradiol;
(e) about 24 mass % of FLUX REMOVER AMS; and
(f) the balance, DMAC solvent.

The second composition was applied onto the dried primer layer to form a drug-polymer layer, using the same spraying technique and equipment used for applying the primer layer. The total amount of solids of the drug-polymer layer was about 720 μg.

A third composition was prepared by mixing the following components:
(g) about 1.0 mass % of PBMA;
(h) about 6 mass % of acetone;
(i) about 43 mass % of FLUX REMOVER AMS; and
(j) the balance of xylene.

The third composition was applied onto the dried drug-polymer layer to form a topcoat layer. The total amount of solids of the topcoat layer was about 160 μg.

Figure 3:
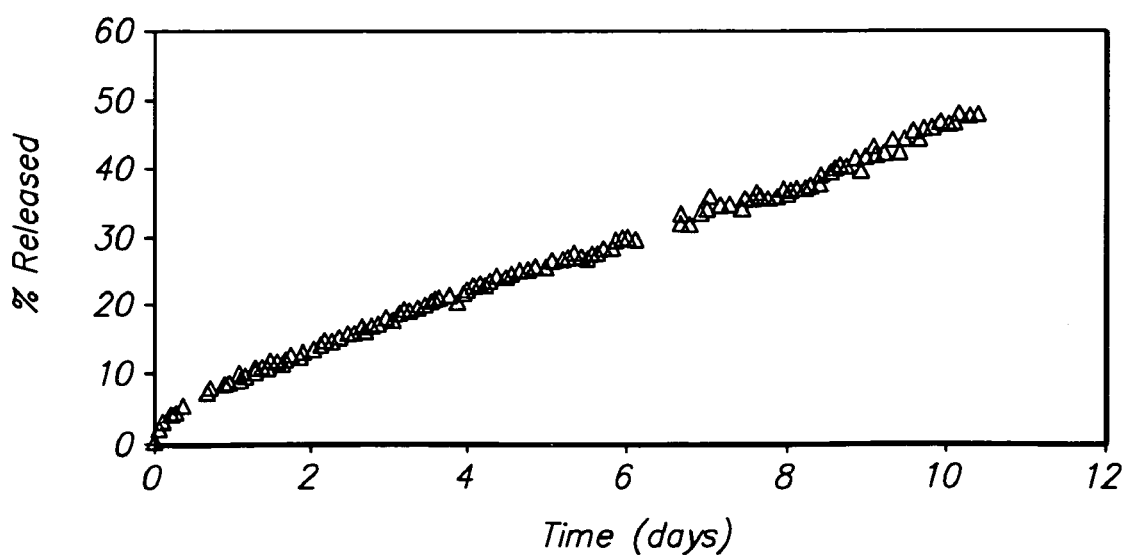
FIGS. 3 and 4 are graphs illustrating the profile of the rate of release of a drug from stents coated according to a method of the present invention.

Stents coated as described above were tested for a kinetic study of the drug release profile. The stents were immersed in a phosphate buffered saline solution having 1 mass % of sodium dodecyl sulfate. A sample of the solution was taken every 20 minutes and analyzed chromatographically (by HPLC) for the amount of estradiol released. As seen from the release profile for three different coated stents shown on FIG. 3, after 10 days 50 mass % of estradiol was released in an almost perfect linear profile indicating a topcoat membrane layer-controlled zero-order type of release. The small burst in the first 24 hours is due to the saturation of the topcoat membrane layer with the drug. Once a stable state was established, the release rate remained constant for 240 hours. The linear correlation coefficient between 24 and 240 hours was 0.997.

Example 2

A first composition was prepared by mixing the following components:
(a) about 2.0 mass % of EVAL;
(b) the balance, DMAC solvent.

The first composition was applied onto the surface of a bare 12 mm stent as in Example 1. The total amount of solids of the primer layer was about 40 μg.

A second composition was prepared by mixing the following components:
(c) about 3.0 mass % of EVAL;
(d) about 1.5 mass % of etoposide;
(e) about 24 mass % of FLUX REMOVER AMS; and
(f) the balance, DMAC solvent.

The second composition was applied onto the dried primer layer to form a drug-polymer layer using the spraying technique and equipment described in Example 1. The total amount of solids of the drug-polymer layer was about 720 μg.

A third composition was prepared by mixing the following components:
(g) about 1.0 mass % of PBMA;
(h) about 6 mass % of acetone;
(i) about 43 mass % of FLUX REMOVER AMS; and
(j) the balance of xylene.

The third composition was applied onto the dried drug-polymer layer to form a topcoat layer. The total amount of solids of the topcoat layer was about 160 μg.

Figure 4:
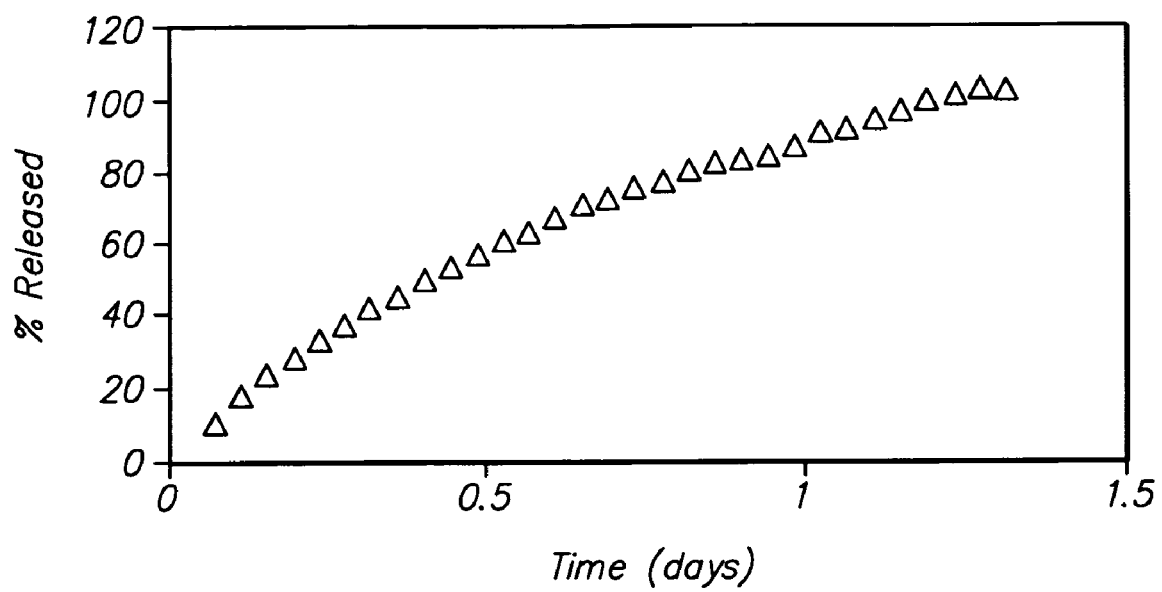

Stents coated as described above were tested for a kinetic study of the drug release profile. The stents were immersed in a phosphate buffered saline solution without sodium dodecyl sulfate. The release rate profile was obtained using the analytical method described Example 1. As seen from the release profile for three different coated stents shown on FIG. 4, the profile was close to linear with a slight downward curvature attributable to some degradation of etoposide in the saline solution.

Example 3

A first composition can be prepared by mixing the following components:
a) between about 0.1 mass % and about 15 mass %, for example, about 2.0 mass % of EVAL;
(b) between about 0.05 mass % and about 1.0 mass %, for example, about 0.7 mass % of estradiol; and
(c) the balance, DMAC solvent.

The first composition can be applied onto a stent as described in Example 1, to form a drug-polymer layer with about 100 μg of total solids.

A second composition can be prepared by mixing the following components:
(d) between about 0.1 mass % and about 15 mass %, for example, about 2.0 mass % of EVAL; and
(e) the balance a solvent mixture, the mixture including DMAC and EtOH in a mass ratio of about 7:3.

The second composition can be applied onto the dried drug-polymer layer, for example, by spraying or dipping, to form a topcoat layer. The topcoat membrane layer can have, for example, a total solids weight of about 500 μg.

Example 4

A first composition can be prepared by mixing the following components:
(a) between about 5 mass % and about 20 mass %, for example, about 12.7 mass % of EVAL;
(b) between about 2 mass % and about 10 mass %, for example, about 4.2 mass % of etoposide; and
(c) the balance, a solvent mixture, the mixture including DMAC and DMSO with the mass ratio of about 5.3:1.

The first composition can be applied onto a stent using the spraying technique and equipment described in Example 1 to form a drug-polymer layer with about 100 μg of total solids.

A second composition can be prepared by mixing the following components:
(d) between about 0.1 mass % and about 15 mass %, for example, about 1.34 mass % of EVAL;
(e) between about 0.1 mass % and about 15 mass %, for example, about 1.21 mass % of PBMA; and
(f) the balance, a solvent mixture, the mixture including DMAC and EtOH with the mass ratio of about 1.3:1.

The second composition can be applied onto the dried drug-polymer layer, for example, using the spraying technique and equipment described in Example 1, to form a topcoat layer having a total solids weight of about 500 µg.

Example 5

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of estradiol; and
(c) the balance, DMAC solvent.

The first composition can be applied onto a stent using the spraying technique and equipment described in Example 1 to form a drug-polymer layer with about 100 µg of total solids.

A second composition can be prepared by mixing the following components:
(d) between about 0.1 mass % and about 15 mass %, for example, about 4.33 mass % of EVAL;
(e) between about 0.1 mass % and about 15 mass %, for example, about 0.93 mass % of BIONATE polymer; and
(f) the balance, a solvent mixture, the mixture including DMSO, THF and DMAC with the mass ratio of about 12.6:10.5:1.

The second composition can be applied onto the dried drug-polymer layer, to form a topcoat layer having a total solids weight of about 500 µg.

Example 6

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of etoposide; and
(c) the balance, DMAC solvent.

The first composition can be applied onto a stent to form a drug-polymer layer with about 100 µg of total solids.

A second composition can be prepared by mixing the following components:
(d) between about 0.1 mass % and about 15 mass %, for example, about 1.3 mass % of EVAL;
(e) between about 0.1 mass % and about 15 mass %, for example, about 0.7 mass % of PBMA; and
(f) the balance, a solvent mixture, the mixture including DMAC and cyclohexanone with the mass ratio of about 5.1:1.

The second composition can be applied onto the dried drug-polymer to form a topcoat layer having a total solids weight of about 500 µg.

Example 7

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of estradiol; and
(c) the balance, DMAC solvent.

The first composition can be applied onto a stent to form a drug-polymer layer with about 100 µg of total solids.

A second composition can be prepared by mixing the following components:
(d) between about 0.1 mass % and about 15 mass %, for example, about 1.3 mass % of EVAL;
(e) between about 0.1 mass % and about 15 mass %, for example, about 0.7 mass % of PBMA; and
(f) the balance, a solvent mixture, the mixture including DMAC and cyclohexanone with the mass ratio of about 5.1:1.

The second composition can be applied onto the dried drug-polymer layer to form a topcoat membrane having a total solids weight of about 500 µg.

A third composition can be prepared by mixing the following components:
(g) between about 0.1 mass % and about 15 mass %, for example, about 2.0 mass % of EVAL;
(h) the balance, DMAC solvent.

The third composition can be applied onto the dried topcoat membrane to form a finishing coat layer having a total solids weight of about 500 µg.

Example 8

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of etoposide; and
(c) the balance, DMAC solvent.

The first composition can be applied onto a stent using to form a drug-polymer layer with about 100 µg of total solids.

A second composition can be prepared by mixing the following components:
(d) between about 0.1 mass % and about 15 mass %, for example, about 4.33 mass % of EVAL;
(e) between about 0.1 mass % and about 15 mass %, for example, about 0.93 mass % of BIONATE polymer; and
(f) the balance, a solvent mixture, the mixture including DMSO, THF and DMAC with a mass ratio of about 12.6:10.5:1.

The second composition can be applied onto the dried drug-polymer layer to form a topcoat layer having a total solids weight of about 500 µg.

A third composition can be prepared by mixing the following components:
(g) between about 0.1 mass % and about 15 mass %, for example, about 2.0 mass % of EVAL;
(h) the balance, DMAC solvent.

The third composition can be applied onto the dried topcoat membrane layer to form a finishing coat layer having a total solids weight of about 500 µg.

Example 9

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of estradiol; and
(c) the balance, DMAC solvent.

The first composition can be applied onto a stent to form a drug-polymer layer with about 100 µg of total solids.

A second composition can be prepared by mixing the following components:

(d) between about 0.1 mass % and about 15 mass %, for example, about 1.5 mass % of PVDF; and (e) the balance, DMAC solvent.

The second composition can be applied onto the dried drug-polymer layer to form a topcoat layer having a total solids weight of about 500 μg.

A third composition can be prepared by mixing the following components:

(g) between about 0.1 mass % and about 15 mass %, for example, about 2.0 mass % of EVAL;

(h) the balance, DMAC solvent.

The third composition can be applied onto the dried topcoat to form a finishing coat layer having a total solids weight of about 500 μg.

Example 10

A composition was prepared by mixing the following components: about 2.0 mass % PBMA; about 1.6 mass % EVEROLIMUS (available from Novartis); and the balance, a solvent mixture, the mixture including about 60 mass % acetone and about 40 mass % xylene. To prepare the composition, PBMA was dissolved in acetone to make the solution having mass concentration of PBMA of about 16.3 mass %, followed by adding the acetone, EVEROLIMUS and xylene and stirring the solution until PBMA and EVEROLIMUS are completely dissolved. About 630 μg of the wet first composition was applied onto the surface of a bare 3 by 18 mm VISION stent using the spraying technique and equipment described in Example 1, to form the drug-polymer layer. The drug-polymer layer was then dried at about 80° C. for about 30 minutes.

Example 11

A stent was coated with a drug-polymer coating as described in Example 10. A composition was prepared by mixing the following components: about 2.0 mass % PBMA; and the balance, a solvents mixture, the mixture including about 27 mass % acetone and about 73 mass % xylene. To prepare the composition, PBMA was dissolved in acetone to make the solution having mass concentration of PBMA of about 16.3 mass %, followed by adding the solvent and stirring the solution until PBMA is completely dissolved. The composition was applied onto the dried drug-polymer layer, using the spraying technique and equipment described in Example 1, followed by drying at about 80° C. for about 30 minutes to form a topcoat membrane layer having a total solids weight of about 20 μg.

Example 12

A stent was coated as described in Example 11, except the topcoat layer had a total solids weight of about 40 μg. The stent coatings prepared in Examples 11 and 12 were tested for the release rate by the method of immersion in a 1% triton X-100-PBS buffered solution. The stent coating of Example 10 (without the topcoat layer) served as the basis for comparison. After 24 hours, the stent of Example 10 released about 18 mass % of EVEROLIMUS, while the stent made in accordance with Example 11 released about 10.3% of EVEROLIMUS, and the stent made in accordance with Example 12 released only about 9.3% of EVEROLIMUS.

The Examples 1–12 are summarized in Table 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

TABLE 1

A Summary of the Formulations of Examples 1–12

| Example | Polymer in drug-polymer layer | Drug in drug-polymer layer | Solvent(s) in drug-polymer layer | Polymer in the topcoat membrane layer | Solvent(s) in the topcoat membrane layer | Polymer in the finishing coat layer | Solvent(s) in the finishing coat layer |
|---|---|---|---|---|---|---|---|
| 1 | EVAL, 3% | Estradiol, 1.5% | Flux Remover AMS, 24% DMAC, 71.5% | PBMA, 1% | Xylene, 50% Flux Remover AMS, 43% Acetone, 6% | N/A | N/A |
| 2 | EVAL, 3% | Etoposide, 1.5% | Flux Remover AMS, 24% DMAC, 71.5% | PBMA, 1% | Xylene, 50% Flux Remover AMS, 43% Acetone, 6% | N/A | N/A |
| 3 | EVAL, 2% | Estradiol, 0.7% | DMAC, 97.3% | EVAL, 2% | DMAC, 49% EtOH, 49% | N/A | N/A |
| 4 | EVAL, 12.7% | Etoposide, 4.2% | DMAC, 70% DMSO, 13.1% | EVAL, 1.34% PBMA, 1.21% | DMAC, 55% EtOH, 42.45% | N/A | N/A |
| 5 | EVAL, 2% | Estradiol, 0.7% | DMAC, 97.3% | EVAL, 4.33% BIONATE, 0.93% | DMSO, 47.16% THF, 39.18% DMAC, 3.73% | N/A | N/A |
| 6 | EVAL, 2% | Etoposide, 0.7% | DMAC, 97.3% | EVAL, 1.3% PBMA, 0.7% | DMAC, 82% Cyclohexanone, 16% | N/A | N/A |
| 7 | EVAL, 2% | Estradiol, 0.7% | DMAC, 97.3% | EVAL, 1.3% PBMA, 0.7% | DMAC, 82% Cyclohexanone, 16% | EVAL, 2% | DMAC, 98% |
| 8 | EVAL, 2% | Etoposide, 0.7% | DMAC, 97.3% | EVAL, 4.33% BIONATE, 0.93% | DMSO, 47.16% THF, 39.18% DMAC, 3.73% | EVAL, 2% | DMAC, 98% |
| 9 | EVAL, 2% | Estradiol, 0.7% | DMAC, 97.3% | PVDF, 1.5% | DMAC, 98.5% | EVAL, 2% | DMAC, 98% |

TABLE 1-continued

A Summary of the Formulations of Examples 1–12

| Example | Polymer in drug-polymer layer | Drug in drug-polymer layer | Solvent(s) in drug-polymer layer | Polymer in the topcoat membrane layer | Solvent(s) in the topcoat membrane layer | Polymer in the finishing coat layer | Solvent(s) in the finishing coat layer |
|---|---|---|---|---|---|---|---|
| 10 | PBMA, 2% | EVEROLIMUS, 1.6% | Acetone, 57.8% Xylene, 38.6% | N/A | N/A | N/A | N/A |
| 11/12*) | PBMA, 2% | EVEROLIMUS, 1.6% | Acetone, 57.8% Xylene, 38.6% | PBMA, 2% | Acetone, 57.8% Xylene, 38.6% | N/A | N/A |

*)Example 11 - the topcoat membrane having about 20 μg of total solids; Example 12 - about 40 μg of total solids

What is claimed is:

1. A method for coating an implantable medical device, comprising:
    (a) forming a first layer on the device, the first layer comprising a first polymer and a therapeutic substance; and
    (b) applying a formulation on the first layer to form a second layer, the formulation comprising a second polymer and a solvent, wherein the solubility of the therapeutic substance in the solvent is less than about 1.0 mass % at room temperature.

2. The method of claim 1, wherein the medical device is a stent.

3. The method of claim 1, wherein the first polymer is poly(ethylene-co-vinyl alcohol).

4. The method of claim 1, wherein the therapeutic substance is for the treatment of restenosis.

5. The method of claim 1, wherein the second polymer is selected from a group consisting of poly(butyl methacrylate), poly(ethyl methacrylate), poly(2-ethylhexyl methacrylate), poly(ethylene-co-vinyl acetate), poly(vinylidenefluoride), polyurethane-polysiloxane block copolymer, styrene-ethylene-butylene-styrene block copolymer, poly carbonate urethane and blends thereof.

6. The method of claim 1, wherein the formulation has a surface tension of about 15 to about 30 dynes/cm$^2$ and a Weber number of about 2,500 to about 45,000.

7. The method of claim 1, further comprising that the second polymer is hydrophobic.

8. The method of claim 7, wherein the second polymer has a solubility parameter in water of less than 11 (cal/cm$^3$)$^{1/2}$.

9. The method of claim 7, wherein the second polymer is selected from a group consisting of poly(butyl methacrylate), poly(ethyl methacrylate), poly(2-ethylhexyl methacrylate), poly(ethylene-co-vinyl acetate), poly(vinylidene fluoride), polyurethane-polysiloxane block copolymer, styrene-ethylene-butylene-styrene block copolymer, poly carbonate urethane polymer and blends thereof.

10. The method of claim 7 wherein the medical device is a stent.

11. The method of claim 7 wherein the first polymer is poly(ethylene-co-vinyl alcohol).

12. The method of claim 7 wherein the therapeutic substance is for the treatment of restenosis.

13. A method for coating an implantable medical device, comprising:
    (a) forming a first layer on the device, the first layer comprising a first polymer and a therapeutic substance; and
    (b) applying a formulation including a solvent and a second polymer on the first layer to form a second layer, wherein the second polymer is more hydrophobic than the first polymer and the solubility of the therapeutic substance in the solvent is less than about 1.0 mass percent at room temperature.

14. The method of claim 13, wherein the device is a stent.

15. The method of claim 13, wherein the second polymer has a solubility parameter in water of less than about 11 (cal/cm$^3$)$^{1/2}$.

16. The method of claim 13, wherein the second polymer is selected from a group consisting of poly(butyl methacrylate), poly(ethyl methacrylate), poly(2-ethylhexyl methacrylate), poly(ethylene-co-vinyl acetate), poly(vinylidene fluoride), polyurethane-polysiloxane block copolymer, styrene-ethylene-butylene-styrene block copolymer, poly carbonate urethane polymer and blends thereof.

17. The method of claim 13, wherein the formulation has a surface tension of about 15 to about 30 dynes/cm$^2$ and a Weber number of about 2,500 to about 45,000.

18. The method of claim 13 wherein the first polymer is poly(ethylene-co-vinyl alcohol).

19. The method of claim 13 wherein the therapeutic substance is for the treatment of restenosis.

* * * * *